(12) United States Patent
Freis et al.

(10) Patent No.: US 7,722,901 B2
(45) Date of Patent: May 25, 2010

(54) USES FOR THE EXTRACT OF A PLANT OF THE FAMILY ASCLEPIADACEAE

(75) Inventors: Olga Freis, Seichamps (FR); Louis Danoux, Saulxures les Nancy (FR); Philippe Moser, Essey-les-Nancy (FR); Gilles Pauly, Nancy (FR)

(73) Assignee: Cognis IP Management GmbH, Duesseldorf (DE)

( * ) Notice: Subject to any disclaimer, the term of this patent is extended or adjusted under 35 U.S.C. 154(b) by 645 days.

(21) Appl. No.: 10/585,423

(22) PCT Filed: Jan. 7, 2005

(86) PCT No.: PCT/EP2005/000076

§ 371 (c)(1),
(2), (4) Date: Jul. 7, 2006

(87) PCT Pub. No.: WO2005/067953

PCT Pub. Date: Jul. 28, 2005

(65) Prior Publication Data

US 2008/0102143 A1    May 1, 2008

(30) Foreign Application Priority Data

Jan. 16, 2004  (EP)  .................................. 04290119

(51) Int. Cl.
*A01N 65/00* (2006.01)
*A61K 36/27* (2006.01)
*A61Q 7/02* (2006.01)

(52) U.S. Cl. ........................ 424/725; 424/70.1; 424/74; 514/880

(58) Field of Classification Search .................. None
See application file for complete search history.

(56) References Cited

U.S. PATENT DOCUMENTS

| | | | |
|---|---|---|---|
| 5,468,476 A | 11/1995 | Ahluwalia et al. | |
| 5,674,477 A | 10/1997 | Ahluwalia | |
| 5,753,612 A | 5/1998 | Mitrani | |
| 6,121,269 A | 9/2000 | Henry et al. | |
| 6,235,737 B1 | 5/2001 | Styczynski et al. | |
| 6,248,751 B1 | 6/2001 | Ahluwalia et al. | |
| 6,294,190 B1 * | 9/2001 | Nakahara et al. | |
| 6,299,865 B1 | 10/2001 | Styczynski et al. | |
| 6,379,673 B1 | 4/2002 | Diwan et al. | |
| 2005/0220726 A1 | 10/2005 | Pauly et al. | |

FOREIGN PATENT DOCUMENTS

| | | | |
|---|---|---|---|
| CN | 1322539 A * | 11/2001 | |
| EP | 0 711 541 A1 | 5/1996 | |
| EP | 711541 A1 * | 5/1996 | |
| EP | 0 700 282 B1 | 7/1998 | |
| EP | 0 943 311 A2 | 9/1999 | |
| EP | 1 074 240 A2 | 2/2001 | |
| EP | 0 700 288 B1 | 7/2001 | |
| FR | 2 753 375 A1 | 3/1998 | |
| JP | 1-258623 A | 10/1989 | |
| JP | 01258623 A * | 10/1989 | |
| JP | 2-207012 A | 8/1990 | |
| JP | 2-292208 A | 12/1990 | |
| JP | 4-26627 A | 1/1992 | |
| JP | 05286841 A * | 11/1993 | |
| JP | 2001-226274 A | 8/2001 | |
| WO | WO 92/00069 A1 | 1/1992 | |
| WO | WO 95/24181 A1 | 9/1995 | |
| WO | WO 95/24885 A1 | 9/1995 | |
| WO | WO 96/09806 A2 | 4/1996 | |
| WO | WO 96/26712 A2 | 9/1996 | |
| WO | WO 98/02134 A1 | 1/1998 | |
| WO | WO 99/62465 A1 | 12/1999 | |
| WO | WO 00/50002 A1 | 8/2000 | |
| WO | WO 01/17486 A2 | 3/2001 | |
| WO | WO 01/72266 A1 | 10/2001 | |
| WO | WO 01/74317 A1 | 10/2001 | |
| WO | WO 03/074013 A1 | 9/2003 | |

OTHER PUBLICATIONS http://www.botany.hawaii.edu/faculty/carr/asclepiad.htm. Asclepiadaceae. Downloaded Jun. 16, 2008.*
Everist, SI. Queensland Agricultural Journal (1962); 88(4): 235-242. These plants can poison people.*
Fushiki, T et al. Journal of Nutrition (1992); 122(12): 2367-2373. An extract of *Gymnema sylvestre* leaves and purified gymnemic acid inhibits glucose-stimulated gastric inhibitory peptide secretion in rats.*
Wang, L. F. et al. Canadian Journal of Physiology and Pharmacology (1998); 76(10-11): 1017-1023. Inhibitory effect of gymnemic acid on intestinal absorption of oleic acid in rats.*
Baskaran et al., "Antidiabetic Effect of a Leaf Extract From *Gymnema sylvestre* in Non-Insulin-Dependent Diabetes Mellitus Patients", Journal of Ethnopharmacology, vol. 30, (1990), pp. 295-305.
Kurihara, "Inhibition of Cyclic 3',5'-Nucleotide Phosphodiesterase in Bovine Taste Papillae by Bitter Taste Stimuli", FEBS Letters, vol. 27, No. 2, (Nov. 1972), pags. 279-281.
Hoffmann, et al., "Interleukin-1β-Induced Inhibition Of Hair Growth In Vitro Is Mediated By Cyclic AMP", The Journal of Investigative Dermatology, vol. 108, No. 1, (Jan. 1997), pp. 40-42.
Rusting, "Hair Why It Grows Why It Stops", Scientific American, vol. 284, No. 6, (2001), pp. 55-63.
Sawaya, "Regulation Of The Human Hair Cycle", Curr. Probl. Dermatol., vol. 13, No. 3, (May/Jun. 2001), pp. 206-210.

(Continued)

*Primary Examiner*—Michele Flood

(57) ABSTRACT

A composition including (a) an extract from a plant of the Asclepiadaceae family; and (b) at least one auxiliary and/or additive, and methods for treating hair growth including administering to a mammal a composition comprising an effective amount of an extract from a plant of the Asclepiadaceae family are provided.

7 Claims, No Drawings

OTHER PUBLICATIONS

Harmon et al., "IL-1α Inhibits Human Hair Follicle Growth And Hair Fiber Production In Whole-Organ Cultures", Lymphokine and Cytokine Research, vol. 12, No. 4, (1993), pp. 197-203.

Groves et al., "Analysis of Epidermal IL-1 Family Members In Vivo Using Transgenic Mouse Models", The Journal of Investigative Dermatology, vol. 102, (1994), p. 556 (SID Abstracts).

Hoffmann et al., "Does Interleukin-1 Induce Hair Loss?", Dermatology, vol. 191, (1995), pp. 273-275.

Shirakawa et al., "Cyclic AMP—An Intracellular Second Messenger For Interleukin 1", Proc. Natl. Acad. Sci. USA, vol. 85, (Nov. 1988), pp. 8201-8205.

Bradford, "A Rapid And Sensitive Method For The Quantitation Of Microgram Quantities Of Protein Utilizing The Principle Of Protein-Dye Binding", Analytical Biochemistry, vol. 72, (1976), pp. 248-254.

Philpott et al., "Human Hair Growth In Vitro", Journal of Cell Science, vol. 97, (1990), pp. 463-471.

* cited by examiner

USES FOR THE EXTRACT OF A PLANT OF THE FAMILY ASCLEPIADACEAE

RELATED APPLICATIONS

This national phase application is filed under 35 U.S.C. §371 from International Application No. PCT/EP2005/000076 filed Jan. 7, 2005, which designated the United States of America and which claims priority from European application EP 04290119.9 filed Jan. 16, 2004; the entire contents of each application are hereby incorporated herein by reference.

FIELD OF THE INVENTION

The present invention relates generally to an extract of a plant, whereby the plant belongs to the family Asclepiadaceae, and more particularly, relates to a composition including the extract and methods of treating hair growth.

BACKGROUND INFORMATION

One of the main functions of hair is to protect the body against negative impact from the environment. This is true for animals. In the case of human hair this function has become almost completely obsolete. Human hair is frequently removed from the human body for cosmetic reasons. On the human scalp the hair is desired to be thick. On other parts of the body this is not a case. Very often hair is unwanted on other parts of the body, especially on the legs, under the arms and on the face. Mechanical removal of hair is traumatic to the skin. Thus it is desirable to reduce the velocity of hair growth in order to make mechanical removal less frequently.

Furthermore there are pathological hair growth disorders (e.g. hirsutism, folliculitis, pseudofolliculitis barbea) that require medical treatment.

U.S. Pat. No. 5,753,612 discloses a method for inhibiting hair growth by administration of activin or activin agonists. A mixture containing activin A or derivatives of activin A and its use to suppress hair follicle cell proliferation is disclosed.

WO 01/74317 discloses methods of modulating hair growth. The methods include modulating VEGF (Vascular Epidermal Growth Factor) activity, e.g. modulating VEGF gene expression and/or modulating VEGF protein production and/or activity to modulate hair growth and hair thickness. The method can be used to either promote or inhibit hair growth or hair thickness.

EP-A 0 700 282 discloses a cosmetic process of reducing mammalian hair growth, comprising selecting an area of skin on which reduced hair growth is desired and applying to said area of skin a composition including an inhibitor of 5-lipoxygenase in an amount effective to reduce hair growth.

According to U.S. Pat. No. 6,121,269 mammalian hair growth is reduced by applying to the skin an inhibitor of protein—tyrosine kinase.

According to WO 96/09806 mammalian hair growth is reduced by applying to the skin a composition including an inhibitor of protein kinase C.

According to WO 92/00069 the rate and character of mammalian hair growth is altered by applying topically to the skin a composition containing an inhibitor of the enzyme gamma-glutamyl transpeptidase.

FR-A 2 753 375 discloses that a sulfotransferase inhibitor reduces and prevents the regrowth of hair.

According to U.S. Pat. No. 5,468,476 mammalian hair growth is reduced by applying to the skin an inhibitor of nitric oxide synthetase.

WO 98/02134 discloses the utilization of serine proteases and their ability to induce programmed cell death and apoptosis in the follicular papillae to affect changes in mammalian hair growth.

According to U.S. Pat. No. 6,299,865 mammalian hair growth is reduced by applying to the skin an inhibitor of alkaline phosphatase other than cromoglycate or a salt thereof.

EP-A 0 943 311 discloses a method of inhibiting hair growth, which comprises administering an inhibitor of elastase-like enzymes or a neutral endopeptidase inhibitor. EP-A 0 943 311 also discloses the use of an inhibitor of elastase-like enzymes or of a neutral endopeptidase inhibitor for the preparation of a hair-growth inhibitor.

According to WO 99/62465 hair growth is reduced by inhibiting the activity of a matrix metalloproteinase in the skin.

EP-A 0 754 024 discloses the application to the skin area of a composition of an ornithine amino transferase inhibitor in a quantity efficient to reduce hair regrowth.

EP-A 1 074 240 discloses a method for reducing hair growth, hair follicle and hair shaft size and hair pigmentation. It comprises the use of one or more substances obtained from the botanical family leguminosae, solanacae, graminacae and curcubitacae. The substances contain one or more serine protease inhibiting compounds and antiandrogenic isoflavones.

EP-A 0 750 489 discloses the inhibition of hair growth by applying an inhibitor of a cysteine pathway enzyme.

EP-A 0 700 288 discloses a cosmetic process of inhibiting mammalian hair growth, comprising the application to the skin of a composition including an inhibitor of cyclooxygenase.

U.S. Pat. No. 6,248,751 discloses a process for inhibiting mammalian hair growth comprising the application of a composition containing a cyclooxygenase inhibitor.

WO 200050002 (U.S. Pat. No. 6,121,269) discloses a method of reducing hair growth comprising the application of a composition comprising a protein-tyrosine kinase inhibitor.

WO 01/72266 discloses cosmetic compositions having retarding action on the regrowth of superfluous hair. These compositions contain fatty acids and antiandrogenic sterols from serenoa (Serenoa repens) and/or from *Cucurbita* seeds (*Cucurbita pepo*).

EP-A 0 711 541 discloses a composition (e.g. a solution) for inhibiting hair growth in mammals which contains as active ingredient a compound which blocks glucose transfer across the membranes of the cells of hair follicles. According to EP-A 0 711 541 a preferred embodiment is the use of phloretin as a glucose blocking compound. Other embodiments are the use of steviol, cytochlasin B, 3,3' diallylstilbesterol and 3,3'-di-(2-chlorallyl)-stilbesterol.

WO 96/26712 discloses a method of inhibiting hair growth that includes applying a dermatologically acceptable composition containing a non-steroidal suppressor of angiogenesis.

According to U.S. Pat. No. 5,674,477 mammalian hair growth is reduced by applying to the skin a dermatologically acceptable composition including a catechin compound.

According to U.S. Pat. No. 6,235,737 mammalian hair growth is reduced by applying to the skin a composition that increases cellular ceramide levels.

U.S. Pat. No. 6,379,673 discloses an herbal formulation for therapeutic and cosmetic applications for the treatment of general skin disorders that contains an aqueous extract of *Gymnena sylvestre*.

JP-A 2001 226 274 discloses a lipase inhibitor that comprises a crude drug or its extract such as guava leaf (*Psidium guajava*), hop (*Humulus lupulus*), *Apocynum venetum* leaf,

*Gymnema* leaf (*Gymnema sylvestre*), and/or *Gardenia fructus* (*Gardenia jasminoides* var. *grandiflora*). The lipase inhibitor according to JP-A 2001 226 274 has the following functions: anorectic, antidiabetic, antilipemic and hypotensive.

WO 01/17486 discloses a method for the cosmetic treatment of skin impairments and baldness by applying deanol or derivatives thereof (deanol is dimethylaminoethanol).

JP-A 2292208 discloses a cosmetic preparation that contains substances obtained from leaves of *Gymnema sylvestre*, *Zizyphus jujuba*, bark and peelings of *Malus pumila* and further substances.

JP-A 02292208 discloses a cosmetic preparation that contains substances obtained from leaves of *Gymnema sylvestre*. The substances are obtained by extraction. The solvent used for extraction is water, alcohol, or mixtures of water and alcohol. The cosmetic preparation according to JP-A 02292208 can be used for the treatment of blotches and freckles.

JP-A 01258623 discloses a composition that stimulates hair growth and blood circulation and prevents baldness. It contains chitin and chitosan in combination with hydrolysing enzymes, organic acids, and substances of *Gymnema sylvestre* and Isagol (hemicellulose of Plantag).

*Gymnema sylvestre* (Retz.) R. Br. ex Schult (belonging to the family Asclepiadaceae) is a woody climbing plant that grows in the tropical forests of central and southern India. The leaves are used in herbal medicine preparations. It is an Ayurvedic herb, it used to be known as "destroyer of sugar", because in ancient times Ayurvedic physicians observed that chewing a few leaves of *Gymnema sylvestre* suppressed the taste of sugar. Today it is used all over India for controlling blood sugar (Baskaran K., Kizar Ahamath B., Radha Shanmugasundaram K., Shanmugasundaram E. R., Antidiabetic effect of a leaf extract from *Gymnema sylvestre* in non-insulin-dependent diabetes mellitus patients, J Ethnopharmacol, volume 30, pages 295 to 300, 1990).

The plant *Gymnema sylvestre* contains two resins (one of them is soluble in alcohol), gymnemic acids, saponins, stigmasterol, quercetol, and the amino acid derivatives betaine, choline and trimethylamine.

*Gymnema sylvestre* is stomachic, diuretic, refrigerant, astringent, and tonic. It has been found to increase urine output and reduce hyperglycemia in both animal and human studies.

*Gymnema sylvestre* has been used in India for the treatment of diabetes for over 2,000 years. The primary application was for adult-onset diabetes, a condition for which it continues to be recommended in India today. The leaves of the plant *Gymnema sylvestre* were also used for stomach ailments, constipation, water retention and liver disease (Baskaran K., Kizar Ahamath B., Radha Shanmugasundaram K., Shanmugasundaram E. R., Antidiabetic effect of a leaf extract from *Gymnema sylvestre* in non-insulin-dependent diabetes mellitus patients, J Ethnopharmacol, volume 30, pages 295 to 300, 1990).

The extract of the plant *Gymnema sylvestre* contains gymnemic acids, flavonoids and phenolic acids. Phenolic acids are acids that have a hydroxybenzene moiety in their structure, e.g. p-hydroxybenzoic acid, protocatechuic acid, vanilic acid, gallic acid, caffeic acid, p-coumaric acid, ferulic acid.

The inhibiting activity of phosphodiesterase (in bovine taste papillae) (and consequently an increase in cAMP) for gymnemic acids is known (Kurihara K., Inhibition of cyclic 3'5'-nucleotide phosphodiesterase in bovine taste papillae by bitter taste stimuli, FEBS Letters, volume 27, pages 279 to 281, 1972). The enzyme phosphodiesterase increases the content of cAMP and there is a hypothesis that hair growth inhibition may be regulated through this pathway (see also: Hoffmann R. et. al., Interleukin-1β-induced inhibition of hair growth in vitro is mediated by cyclic AMP, J. Invest. Dermatol., volume 108, pages 40 to 42, 1997).

The factors that influence the growth of hair follicles are not completely known. It is known that numerous growth factors (cytokines, receptors and hormones) are critical for their development (Rusting R. L., Scientific American, volume 284, pages 55 to 63, 2001 and Sawaya, Curr. Probl. Dermatol., volume 13, pages 206 to 210, 2001).

The mechanisms of hair growth have been studied intensively. The regulation of the hair cycle, the problem of baldness and the search for molecules capable to control hair growth are of interest for pharmaceutical and for cosmetic reasons.

The "hair cycle" is the growth of hair in three phases, which are the growing of hair (anagen phase), the weakening of hair (catagen phase) and the falling out of hair (telogen phase). Baldness may be due to the dysfunction of the hair cycle in a way that comprises a shortened anagen phase and a too early entry in the catagen phase, whereby promoters influence this entry in the catagen phase.

Interleukin 1 (IL-1) can inhibit the growth of hair follicles in vitro (Harmon C. S., Nevis T. D., Lymphokine, Cytokine Res., volume 12, pages 197 to 203, 1993).

Transgenic mice that over-express IL-1α in basal keratinocytes show patchy hair loss (Groves R. W. et al., Analysis of epidermal IL-1 family members in vivo using transgenic mouse models, J. Invest. Dermatol., volume 102, page 556, 1994).

IL-1β was found to be expressed aberrantly in active alopecia areata, when the treatment of baldness is based on antagonists of IL-1β mediated intrafollicular pathways leading to the weakening of hair follicles and finally to the loss of hair (Hoffmann R., Happle R., Does Interleukin-1 induce hair loss in vivo? Dermatology, volume 191, pages 273 to 275, 1995).

The signaling pathways of IL-1β induced suppression of hair growth are unknown. Some pharmacological data suggest that IL-1β induced hair growth inhibition is mediated by cAMP (cAMP or cyclic AMP is cyclic adenosine monophosphate) (Hoffmann R. et al, Interleukin-1β-induced inhibition of hair growth in vitro is mediated by cyclic AMP. J. Invest. Dermatol., volume 108, pages 40 to 42, 1997 and Shirakawa F. et al, Cyclic AMP—an intracellular second messenger for interleukin-1, Proc. Natl. Acad. Sci. USA, volume 85, pages 8201 to 8205, 1988).

Il-1 utilizes different signaling pathways, one of them is the cAMP-activated protein kinase pathway.

The role of cAMP in hair follicle cells is not known. It has been assumed that it inhibits the differentiation of matrix cells and that it inhibits cellular proliferation.

The problem underlying the present invention is the need for further substances that can be used to suppress, retard or inhibit hair growth either for medical or for cosmetic reasons.

SUMMARY OF THE INVENTION

According to an aspect of the invention, in one embodiment, a composition includes (a) an extract from a plant of the Asclepiadaceae family; and (b) at least one auxiliary and/or additive.

In another embodiment, according to an aspect of the invention, a method for treating a hair growth disorder in a mammal includes administering to a mammal in need of treatment thereof a composition comprising an effective amount of an extract from a plant of the Asclepiadaceae family.

In another embodiment, according to an aspect of the invention, a method for treating hair growth in a mammal includes administering to a mammal a composition which inhibits hair growth, comprising an effective amount of an extract from a plant of the Asclepiadaceae family.

One embodiment of the present invention is an extract of the plant *Gymnema sylvestre* for use as a medicament. Said medicaments are inter alia useful for the treatment of mammalian skin (preferably human skin) that suffers from hair growth disorders. Furthermore the present invention is concerned with the use of an extract of a plant, whereby the plant belongs to the family Asclepiadaceae (especially *Gymnema sylvestre*) for the cosmetic treatment of human skin, whereby this treatment comprises the inhibition, suppression or retardation of hair growth.

DETAILED DESCRIPTION OF THE INVENTION

According to an aspect of the invention, in one embodiment, a composition includes (a) an extract from a plant of the Asclepiadaceae family; and (b) at least one auxiliary and/or additive.

In another embodiment, according to an aspect of the invention, a method for treating a hair growth disorder in a mammal includes administering to a mammal in need of treatment thereof a composition comprising an effective amount of an extract from a plant of the Asclepiadaceae family.

In another embodiment, according to an aspect of the invention, a method for treating hair growth in a mammal includes administering to a mammal a composition which inhibits hair growth, comprising an effective amount of an extract from a plant of the Asclepiadaceae family.

One aspect of this problem is solved by the use of an extract of a plant, whereby the plant belongs to the family Asclepiadaceae (the plant *Gymnema sylvestre* is preferred) for the manufacture of a medicament for the treatment of mammalian skin (preferably human skin) that suffers from hair growth disorders (e.g. hirsutism, folliculitis, pseudofolliculitis barbea). This use is a subject of the present invention.

Because an extract of a plant, whereby the plant belongs to the family Asclepiadaceae (the plant *Gymnema sylvestre* is preferred) for use as a medicament in general is not known in the state of the art this is a further, more general subject of the present invention.

Another aspect of this problem is solved by the use of a substance selected from the group consisting of an extract of a plant, whereby the plant belongs to the family Asclepiadaceae (the plant *Gymnema sylvestre* is preferred) and a composition comprising an extract of a plant, whereby the plant belongs to the family Asclepiadaceae (the plant *Gymnema sylvestre* is preferred) and auxiliaries and/or additives which are common for cosmetic purposes for the cosmetic treatment of human skin, whereby this treatment comprises the inhibition, suppression or retardation of hair growth. This use is another subject of the present invention.

In one embodiment of the present invention the auxiliaries and/or additives which are common for cosmetic purposes are selected from the group consisting of oily bodies, surfactants, emulsifiers, fats, waxes, pearlescent waxes, bodying agents, thickeners, superfatting agents, stabilizers, polymers, silicone compounds, lecithins, phospholipids, biogenic active ingredients, deodorants, antimicrobial agents, antiperspirants, film formers, antidandruff agents, swelling agents, insect repellents, hydrotropes, solubilizers, preservatives, perfume oils and dyes.

In one embodiment of the present invention the auxiliaries and additives which are common for cosmetic purposes are selected from the group consisting of surfactants, emulsifiers, fats, waxes, stabilizers, deodorants, antiperspirants, antidandruff agents and perfume oils.

The concentration of the extract of the plant in the compositions for cosmetic or for medical applications can vary in wide ranges. In one embodiment of the present invention this concentration is 0.001 weight-%, preferably 0.01 weight-%, more preferably 0.1 weight-% to 50 weight-%, preferably to 10 weight-%, more preferably to 1 weight-%.

The plant *Gymnema sylvestre* belongs to the family Asclepiadaceae. Extracts of *Gymnema sylvestre* and their use for cosmetic purposes in general are known. One method of producing the extract of a plant that belongs to the family Asclepiadaceae (preferably *Gymnema sylvestre*) according to the present invention comprises a) extracting said plant or parts of said plant with a solvent selected from the group consisting of water, an alcohol with 1 to 6 carbon atoms (preferably methanol), a 1,2-alkanediol (preferably 1,2-butanediol or 1,2-pentanediol) and mixtures thereof to obtain a mixture comprising said solvent and said extract, b) removing said solvent from said mixture to obtain said extract.

In one embodiment of the present invention the extract of the plant *Gymnema sylvestre* is used together with an extract of another plant that belongs to the family Asclepiadaceae.

In one embodiment of the present invention the extract of the leaves of the plant *Gymnema sylvestre* is used.

In one embodiment of the present invention the extract of the plant *Gymnema sylvestre* or the combination of the extract of the plant *Gymnema sylvestre* is used in combination with further substances:

e.g. with substances that have anti-inflammatory properties (e.g. Anasensyl® LS 9322 obtainable by Cognis Deutschland GmbH and Co KG, D-40551 Düsseldorf, Germany; INCI names: mannitol and ammonium glycyrrhizate and caffeine and zinc gluconate and *aesculus hippocastanum* (horse chestnut) extract) (or e.g. Cytokinol® LS 9028 obtainable by Cognis Deutschland GmbH und Co KG, D-40551 Düsseldorf, Germany; INCI names: hydrolyzed casein and hydrolyzed yeast protein and lysine hydrochloride).

e.g. with substances that have keratolytic properties (e.g. Pilinhib® VEG LS 9109 obtainable by Cognis Deutschland GmbH und Co KG, D-40551 Düsseldorf, Germany; INCI names: propylene glycol and hydrolyzed soy protein and *hypericum perforatum* extract and *hamamelis virginiana* (witch hazel) extract and *arnica montana* flower extract and urea and *salix alba* (willow) bark extract and menthol and saliclic acid).

In one embodiment of the present invention the extract of the plant *Gymnema sylvestre* or the combination of the extract of the plant *Gymnema sylvestre* is used in combination with sugar esters. Sugar esters have advantageous properties, e.g. fructose caprate has anti-hair-growth activity and some sugar esters have anti-microbial activity that is advantageous in depilatory or post-depilatory compositions.

Cosmetic and pharmaceutical compositions containing sugar esters have been disclosed in WO 03/074013.

Reduced hair growth is desired also in the axilla area, where deodorants and anti-perspirants are used and where the anti-microbial activity of sugar esters in combination with the extracts according to the present invention can be applied.

The auxiliaries and additives which are common for cosmetic purposes can be selected from the group consisting of oily bodies, surfactants, emulsifiers, fats, waxes, pearlescent waxes, bodying agents, thickeners, superfatting agents, stabilizers, polymers, silicone compounds, lecithins, phospholipids, biogenic active ingredients, deodorants, antimicrobial agents, antiperspirants, film formers, antidandruff agents, swelling agents, insect repellents, hydrotropes, solubilizers, preservatives, perfume oils and dyes.

In one embodiment of the present invention the auxiliaries and additives which are common for cosmetic purposes are selected from the group consisting of surfactants, emulsifiers, fats, waxes, stabilizers, deodorants, antiperspirants, antidandruff agents and perfume oils. The total content of auxiliaries and additives may be 1 to 50% by weight, preferably 5 to 40% by weight, based on the cosmetic and/or pharmaceutical preparations or compositions. The preparations can be prepared by customary cold or hot processes; preference is given to using the phase-inversion temperature method.

Application can be topical or oral in the form of tablets, dragees, capsules, juices, solutions and granules.

Surfactants (or Surface-active substances) that may be present are anionic, non-ionic, cationic and/or amphoteric or amphoteric surfactants, the content of which in the compositions is usually about 1 to 70% by weight, preferably 5 to 50% by weight and in particular 10 to 30% by weight. Typical examples of anionic surfactants are soaps, alkylbenzenesulfonates, alkanesulfonates, olefin sulfonates, alkyl ether sulfonates, glycerol ether sulfonates, α-methyl ester sulfonates, sulfo fatty acids, alkyl sulphates, fatty alcohol ether sulphates, glycerol ether sulphates, fatty acid ether sulphates, hydroxy mixed ether sulphates, monoglyceride (ether) sulphates, fatty acid amide (ether) sulphates, mono- and dialkyl sulfosuccinates, mono- and dialkyl sulfosuccinamates, sulfotriglycerides, amide soaps, ether carboxylic acids and salts thereof, fatty acid isethionates, fatty acid sarcinates, fatty acid taurides, N-acylamino acids, e.g. acyl lactylates, acyl tartrates, acyl glutamates and acyl aspartates, alkyl oligoglucoside sulphates, protein fatty acid condensates (in particular wheat-based vegetable products) and alkyl (ether) phosphates. If the anionic surfactants contain polyglycol ether chains, these may have a conventional homologous distribution, but preferably have a narrowed homologous distribution. Typical examples of non-ionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucoronic acid derivatives, fatty acid N-alkylglucamides, protein hydrolysates (in particular wheat-based vegetable products), polyol fatty acid esters, sugar esters, sorbitan esters, polysorbates and amine oxides. If the non-ionic surfactants contain polyglycol ether chains, these may have a conventional homologous distribution, but preferably have a narrowed homologous distribution. Typical examples of cationic surfactants are quaternary ammonium compounds, e.g. dimethyldistearylammonium chloride, and ester quats, in particular quaternized fatty acid trialkanolamine ester salts. Typical examples of amphoteric or zwitterionic surfactants are alkylbetaines, alkylamidobetaines, aminopropionates, aminoglycinates, imidazolinium-betaines and sulfobetaines. Said surfactants are known compounds. With regard to structure and preparation of these substances, reference may be made to relevant review works.

Typical examples of particularly suitable mild, i.e. particularly skin-compatible surfactants are fatty alcohol polyglycol ether sulphates, monoglyceride sulphates, mono- and/or dialkyl sulfosuccinates, fatty acid isethionates, fatty acid sarcosinates, fatty acid taurides, fatty acid glutamates, α-olefinsulfonates, ether carboxylic acids, alkyl oligoglucosides, fatty acid glucamides, alkylamido-betaines, amphoacetals and/or protein fatty acid condensates, the latter preferably based on wheat proteins.

Suitable oily bodies are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, for example myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, coleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxycarboxylic acids with linear or branched $C_6$-$C_{22}$-fatty alcohols, in particular dioctyl malates, esters of linear and/or branched fatty acids with polyhydric alcohols (for example propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, for example dicaprylyl carbonates (Cetiol® CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or unsymmetrical dialkyl ethers having 6 to 22 carbon atoms per alkyl group, for example dicaprylyl ether (Cetiol® OE), ring-opening products of epoxidized fatty acid esters with polyols, silicone oils (cyclomethicones, silicon methicone types, inter alia) and/or aliphatic or naphthenic hydrocarbons, for example squalane, squalene or dialkylcyclohexanes.

Suitable emulsifiers are, for example, nonionogenic surfactants from at least one of the following groups:

addition products of from 2 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group, and onto alkylamines having 8 to 22 carbon atoms in the alkyl radical;

alkyl and/or alkenyl oligoglycosides having 8 to 22 carbon atoms in the alk(en)yl radical and the ethoxylated analogs thereof;

addition products of from 1 to 15 mol of ethylene oxide onto castor oil and/or hydrogenated castor oil;

addition products of from 15 to 60 mol of ethylene oxide onto castor oil and/or hydrogenated castor oil;

partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide;

partial esters of polyglycerol (average degree of self-condensation 2 to 8), polyethylene glycol (molecular weight 400 to 5 000), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide;

mixed esters of pentaerythritol, fatty acids, citric acid and fatty alcohols and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof;

wool wax alcohols;

polysiloxane-polyalkyl-polyether copolymers and corresponding derivatives;

block copolymers, e.g. polyethylene glycol-30 dipolyhydroxystearates;

polymer emulsifiers, e.g. Pemulen® grades (TR-1, TR-2) from Goodrich;

polyalkylene glycols, and glycerol carbonate.

The addition products of ethylene oxide and/or of propylene oxide onto fatty alcohols, fatty acids, alkylphenols or onto castor oil are known, commercially available products. These are homologous mixtures whose average degree of alkoxylation corresponds to the ratio of the amounts of ethylene oxide and/or propylene oxide and substrate with which the addition reaction is carried out. $C_{12/18}$-fatty acid mono- and diesters of addition products of ethylene oxide onto glycerol are known as refatting agents for cosmetic preparations.

Alkyl and/or alkenyl oligoglycosides, their preparation and their use are known from the prior art. They are prepared, in particular, by reacting glucose or oligo-saccharides with primary alcohols having 8 to 18 carbon atoms. With regard to the glycoside radical, both monoglycosides, in which a cyclic sugar radical is glycosidically bonded to the fatty alcohol, and also oligomeric glycosides having a degree of oligomerization of up to, preferably, about 8, are suitable. The degree of oligomerization here is a statistical average value that is based on a homologous distribution customary for such technical-grade products.

Typical examples of suitable partial glycerides are hydroxy stearic acid monoglyceride, hydroxy stearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid mono-glyceride, linoleic acid diglyceride, linoleic acid monoglyceride, linoleic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride, and the technical-grade mixtures thereof which may also comprise small amounts of triglyceride as a minor product of the preparation process. Likewise suitable are addition products of 1 to 30 mol, preferably 5 to 10 mol, of ethylene oxide onto said partial glycerides.

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Likewise suitable are addition products of 1 to 30 mol, preferably 5 to 10 mol, of ethylene oxide onto said sorbitan esters.

Typical examples of suitable polyglycerol esters are polyglyceryl-2 dipolyhydroxystearate (Dehymuls® PGPH), polyglycerol-3 diisostearate (Lameform® TGI), polyglyceryl-4 isostearate (Isolan® GI 34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (Polyglycerol Caprate T2010/90), polyglyceryl-3 cetyl ether (Chimexane® NL), polyglyceryl-3 distearate (Cremophor® GS 32) and polyglyceryl polyricinoleate (Admul® WOL 1403), polyglyceryl dimerate isostearate, and mixtures thereof. Examples of further suitable polyol esters are the mono-, di- and triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like.

Furthermore, zwitterionic surfactants can be used as emulsifiers. The term "zwitterionic surfactants" refers to those surface-active compounds that carry at least one quaternary ammonium group and at least one carboxylate and one sulfonate group in the molecule. Particularly suitable zwitterionic surfactants are the betaines, such as N-alkyl-N,N-dimethylammonium glycinates, for example cocoalkyldimethylammonium glycinate, N-acylaminopropyl-N,N-dimethylammonium glycinates, for example cocoacylaminopropyl-dimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethylcarboxymethyl glycinate. Particular preference is given to the fatty acid amide derivative known under the CTFA name Cocamidopropyl Betaine. Likewise suitable emulsifiers are ampholytic surfactants. The term "ampholytic surfactants" means those surface-active compounds that, apart from a $C_{8/18}$-alkyl or -acyl group in the molecule, contain at least one free amino group and at least one —COOH or —SO$_3$H group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkyl aminopropionate, cocoacylaminoethyl aminopropionate and $C_{12/18}$-acylsarcosine. Finally, cationic surfactants are also suitable emulsifiers, those of the ester quat type, preferably methyl-quaternized difatty acid triethanolamine ester salts, being particularly preferred.

Fats and waxes that can be used are described in the following text. Typical examples of fats are glycerides, i.e. solid or liquid vegetable or animal products which consist essentially of mixed glycerol esters of higher fatty acids, suitable waxes are inter alia natural waxes, for example candelilla wax, carnauba wax, japan wax, esparto grass wax, cork wax, guaruma wax, rice germ oil wax, sugarcane wax, ouricury wax, montan wax, beeswax, shellac wax, spermaceti, lanolin (wool wax), uropygial grease, ceresin, ozokerite (earth wax), petrolatum, paraffin waxes, microcrystalline waxes; chemically modified waxes (hard waxes), for example montan ester waxes, sasol waxes, hydrogenated jojoba waxes, and synthetic waxes, for example polyalkylene waxes and polyethylene glycol waxes. In addition to the fats, suitable additives are also fat-like substances, such as lecithins and phospholipids. The term lecithins is understood by the person skilled in the art as meaning those glycerophospholipids which form from fatty acids, glycerol, phosphoric acid and choline by esterification. Lecithins are thus frequently also referred to as phosphatidylcholines (PC). Examples of natural lecithins which may be mentioned are the cephalins, which are also referred to as phosphatidic acids and represent derivatives of 1,2-diacyl-sn-glycerol-3-phosphoric acids. By contrast, phospholipids are usually understood as meaning mono- and, preferably, diesters of phosphoric acid with glycerol (glycerophosphates), which are generally considered to be fats. In addition, sphingosines and sphingolipids are also suitable.

Examples of suitable pearlescent waxes are: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, for example fatty alcohols, fatty ketones, fatty aldehydes, fatty ethers and fatty carbonates, which have a total of at least 24 carbon atoms, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups, and mixtures thereof.

Bodying agents and thickeners that can be used are described in the following text. Suitable bodying agents are primarily fatty alcohols or hydroxy fatty alcohols having 12 to 22, and preferably 16 to 18, carbon atoms, and also partial glycerides, fatty acids or hydroxy fatty acids. Preference is given to a combination of these substances with alkyl oligoglucosides and/or fatty acid N-methylglucamides of identical chain length and/or polyglycerol poly-12-hydroxystearates. Suitable thickeners are, for example, Aerosil grades (hydrophilic silicas), polysaccharides, in particular xanthan gum, guar guar, agar agar, alginates and Tyloses, carboxymethylcellulose and hydroxyethylcellulose, and also relatively high molecular weight polyethylene glycol mono- and diesters of fatty acids, polyacrylates (e.g. Carbopols® and Pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinylpyrrolidone, surfactants, for example ethoxylated fatty acid glycerides, esters of fatty acids with polyols for example pentaerythritol or trimethylolpropane, fatty alcohol ethoxylates having a narrowed homologue distribution or alkyl oligoglucosides, and electrolytes such as sodium chloride and ammonium chloride.

Superfatting agents which can be used are substances for example lanolin and lecithin, and polyethoxylated or acylated lanolin and lecithin derivatives, polyol fatty acid esters, monoglycerides and fatty acid alkanolamides, the latter also serving as foam stabilizers.

Stabilizers which can be used are metal salts of fatty acids, for example magnesium, aluminium and/or zinc stearate or ricinoleate.

Polymers that can be used are described in the following text. Suitable cationic polymers are, for example, cationic cellulose derivatives, for example a quaternized hydroxyethylcellulose obtainable under the name Polymer JR 400® from Amerchol, cationic starch, copolymers of diallylammonium salts and acryl amides, quaternized vinylpyrrolidone-vinylimidazole polymers, for example Luviquat® (BASF), condensation products of polyglycols and amines, quaternized collagen polypeptides, for example lauryldimonium hydroxypropyl hydrolysed collagen (Lamequat®L/Grünau), quaternized wheat polypeptides, polyethyl-eneimine, cationic silicone polymers, for example amodimethicones, copolymers of adipic acid and dimethylaminohydroxypropyldiethylenetriamine (Cartaretins®/Sandoz), copolymers of acrylic acid with dimethyl diallylammonium chloride (Merquat® 550/Chemviron), polyaminopolyamides and cross linked water-soluble polymers thereof, cationic chitin derivatives, for example quaternized chitosan, optionally in microcrystalline dispersion, condensation products from dihaloalkyls, for example dibromobutane with bisdialkylamines, for example bis-dimethylamino-1,3-propane, cationic guar gum, for example Jaguar® CBS, Jaguar® C-17, Jaguar® C-16 from Celanese, quaternized ammonium salt polymers, for example Mirapol® A-15, Mirapol® AD-1, Mirapol® AZ-1 from Miranol.

Suitable anionic, zwitterionic, amphoteric and nonionic polymers are, for example, vinyl acetate-crotonic acid copolymers, vinylpyrrolidone-vinyl acrylate copolymers, vinyl acetate-butyl maleate-isobornyl acrylate copolymers, methyl vinyl ether-maleic anhydride copolymers and esters thereof, uncrosslinked polyacrylic acids and polyacrylic acids crosslinked with polyols, acrylamido-propyltrimethylammonium chloride-acrylate copolymers, octylacrylamide-methyl methacrylate-tert-butylaminoethyl methacrylate-2-hydroxypropyl methacrylate copolymers, polyvinylpyrrolidone, vinylpyrrolidone-vinyl acetate copolymers, vinylpyrrolidone-dimethylaminoethyl methacrylate-vinylcaprolactam terpolymers, and optionally derivatized cellulose ethers and silicones.

Suitable silicone compounds are, for example, dimethylpolysiloxanes, methylphenylpolysiloxanes, cyclic silicones, and amino-, fatty-acid-, alcohol-, polyether-, epoxy-, fluorine-, glycoside- and/or alkyl-modified silicone compounds, which can either be liquid or in resin form at room temperature. Also suitable are simethicones, which are mixtures of dimethicones having an average chain length of from 200 to 300 dimethylsiloxane units and hydrogenated silicates.

Deodorants and antimicrobial agents that can be used are described in the following text. Cosmetic deodorants counteract, mask or remove body odors. Body odors arise as a result of the effect of skin bacteria on apocrine perspiration, with the formation of degradation products which have an unpleasant odor. Accordingly, deodorants comprise active ingredients which act as antimicrobial agents, enzyme inhibitors, odor absorbers or odor masking agents. Suitable antimicrobial agents are, in principle, all substances effective against gram-positive bacteria, for example 4-hydroxybenzoic acid and its salts and esters, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methylene-bis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorohexidine, 3,4,4'-trichlorocarbanilide (TTC), antibacterial fragrances, thymol, thyme oil, eugenol, oil of cloves, menthol, mint oil, farnesol, phenoxy-ethanol, glycerol monocaprate, glycerol monocaprylate, glycerol monolaurate (GML), diglycerol monocaprate (DMC), salicylic acid N-alkylamides, for example n-octylsalicylamide or n-decylsalicylamide.

Suitable enzyme inhibitors are preferably, for example, esterase inhibitors. These are preferably trialkyl citrates, such as trimethyl citrate, tripropyl citrate, triisopropyl citrate, tributyl citrate and, in particular, triethyl citrate (Hydagen® CAT). The substances inhibit enzyme activity, thereby reducing the formation of odor. Other substances which are suitable esterase inhibitors are sterol sulfates or phosphates, for example lanosterol, cholesterol, campesterol, stigmasterol and sitosterol sulfate or phosphate, dicarboxylic acids and esters thereof, for example glutaric acid, monoethyl glutarate, diethyl glutarate, adipic acid, monoethyl adipate, diethyl adipate, malonic acid and diethyl malonate, hydroxycarboxylic acids and esters thereof, for example citric acid, malic acid, tartaric acid or diethyl tartrate, and zinc glycinate.

Suitable odor absorbers are substances which are able to absorb and largely retain odor-forming compounds. They lower the partial pressure of the individual components, thus also reducing their rate of diffusion. It is important that in this process perfumes must remain unimpaired. Odor absorbers are not effective against bacteria. They comprise, for example, as main constituent, a complex zinc salt of ricinoleic acid or specific, largely odor-neutral fragrances which are known to the person skilled in the art as "fixatives", for example extracts of labdanum or *styrax* or certain abietic acid derivatives. The odor masking agents are fragrances or perfume oils, which, in addition to their function as odor masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal raw materials, for example civet and castoreum. Typical synthetic fragrance compounds are products of the ester, ether, aldehyde, ketone, alcohol and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl sali-cylate. The ethers include, for example, benzyl ethyl ether, and the aldehydes include, for example, the linear alkanals having 8 to 18 carbon atoms, citral, citronellal, citronellyloxyacetaldehyde, cyclamen aldehyde, hydroxycitronellal, lilial and bourgeonal, the ketones include, for example, the ionones and methyl cedryl ketone, the alcohols include anethole, citronellol, eugenol, isoeugenol, geraniol, linalool, phenylethyl alcohol and terpineol, and the hydrocarbons include mainly the terpenes and balsams. Preference is, however, given to using mixtures of different fragrances which together produce a pleasing fragrance note. Ethereal oils of relatively low volatility, which are mostly used as aroma components, are also suitable as perfume oils, e.g. sage oil, camomile oil, oil of cloves, melissa oil, mint oil, cinnamon leaf oil, linden flower oil, juniper berry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Antiperspirants reduce the formation of perspiration by influencing the activity of the eccrine sweat glands, thus counteracting underarm wetness and body odor. Aqueous or anhydrous formulations of antiperspirants typically comprise one or more of the following ingredients: astringent active ingredients, oil components, nonionic emulsifiers, coemulsifiers, bodying agents, auxiliaries, for example thickeners or complexing agents, and/or nonaqueous solvents, for example ethanol, propylene glycol and/or glycerol.

Suitable astringent antiperspirant active ingredients are primarily salts of aluminum, zirconium or of zinc. Such suitable antihydrotic active ingredients are, for example, aluminum chloride, aluminum chlorohydrate, aluminum dichlorohydrate, aluminum sesquichlorohydrate and complex compounds thereof, e.g. with 1,2-propylene glycol, aluminum hydroxyallantoinate, aluminum chloride tartrate, aluminum zirconium trichlorohydrate, aluminum zirconium tetrachlorohydrate, aluminum zirconium pentachlorohydrate and complex compounds thereof, e.g. with amino acids, such as glycine. In addition, customary oil-soluble and water-soluble auxiliaries may be present in antiperspirants in relatively small amounts. Such oil-soluble auxiliaries may, for example, be anti-inflammatory, skin-protective or perfumed ethereal oils, synthetic skin-protective active ingredients and/or oil-soluble perfume oils.

Customary water-soluble additives are, for example, preservatives, water-soluble fragrances, pH regulators, e.g. buffer mixtures, water-soluble thickeners, e.g. water-soluble natural or synthetic polymers, for example xanthan gum, hydroxyethylcellulose, polyvinylpyrrolidone or high molecular weight polyethylene oxides.

Film formers that can be used are described in the following text. Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof, and similar compounds.

Suitable antidandruff active ingredients are piroctone olamine (1-hydroxy-4-methyl-6-(2,4,4-trimethylpentyl)-2-(1H)-pyridinone monoethanolamine salt), Baypival® (climbazole), Ketoconazole®, (4-acetyl-1-{-4-[2-(2,4-dichlorophenyl) r-2-(1H-imidazol-1-ylmethyl)-1,3-dioxylan-c-4-ylmethoxyphenyl}piperazine, ketoconazole, elubiol, selenium disulfide, colloidal sulfur, sulfur polyethylene glycol sorbitan monooleate, sulfur ricinol polyethoxylate, sulfur tar distillates, salicyclic acid (or in combination with hexachlorophene), undecylenic acid monoethanolamide sulfosuccinate Na salt, Lamepon® UD (protein undecylenic acid condensate), zinc pyrithione, aluminum pyrithione and magnesium pyrithione/dipyrithione magnesium sulfate.

The swelling agents for aqueous phases may be montmorillonites, clay mineral substances, Pemulen, and alkyl-modified Carbopol grades (Goodrich).

Suitable insect repellents are N,N-diethyl-m-toluamide, 1,2-pentanediol or ethyl butylacetylaminopropionate.

To improve the flow behavior, hydrotropes, for example ethanol, isopropyl alcohol, or polyols, can be used. Polyols which are suitable here preferably have 2 to 15 carbon atoms and at least two hydroxyl groups. The polyols can also contain further functional groups, in particular amino groups, or be modified with nitrogen. Typical examples are:

glycerol;

alkylene glycols, for example, ethylene glycol, diethylene glycol, propylene glycol, butylene glycol, hexylene glycol, and polyethylene glycols with an average molecular weight of from 100 to 1 000 daltons;

technical-grade oligoglycerol mixtures with a degree of self-condensation of from 1.5 to 10, for example, technical-grade diglycerol mixtures with a diglycerol content of from 40 to 50% by weight;

methylol compounds, such as trimethylolethane, trimethylolpropane, trimethylolbutane, pentaerythritol and dipentaerythritol;

lower alkyl glucosides, in particular those with 1 to 8 carbon atoms in the alkyl radical, for example methyl and butyl glucoside;

sugar alcohols with 5 to 12 carbon atoms, for example sorbitol or mannitol, sugars with 5 to 12 carbon atoms, for example glucose or sucrose;

amino sugars, for example glucamine;

dialcohol amines, such as diethanolamine or 2-amino-1,3-propanediol.

Suitable preservatives are, for example, phenoxyethanol, formaldehyde solution, parabenes, pentanediol or sorbic acid, and the other classes of substance listed in Annex 6, Part A and B of the Cosmetics Directive.

Perfume oils which may be used are preferably mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot, lemon, orange), roots (mace, angelica, celery, cardamom, costus, iris, calmus), woods (pine wood, sandalwood, guaiac wood, cedarwood, rosewood), herbs and grasses (tarragon, lemon grass, sage, thyme), needles and branches (spruce, fir, pine, dwarf-pine), resins and balsams (galbanum, elemi, benzoin, myrrh, olibanum, opoponax). Also suitable are animal raw materials, for example civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tert-butylcyclohexyl acetate, linalyl acetate, dimethylbenzyl-carbinyl acetate, phenylethyl acetate, linalyl benzoate, benzyl formate, ethylmethylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bour-geonal, and the ketones include, for example, the ionones, α-isomethylionone and methyl cedryl ketone, the alcohols include anethole, citronellol, eugenol, isoeugenol, geraniol, linalool, phenylethyl alcohol and terpineol, and the hydrocarbons include predominantly the terpenes and balsams. Preference is, however, given to using mixtures of different fragrances which together produce a pleasing fragrance note. Ethereal oils of relatively low volatility, which are mostly used as aroma components, are also suitable as perfume oils, e.g. sage oil, camomile oil, oil of cloves, melissa oil, mint oil, cinnamon leaf oil, linden blossom oil, juniper berry oil, vetiver oil, olibanum oil, galbanum oil, labolanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evemyl, iraldein gamma, phenylacetic acid, geranyl acetate, benzyl acetate, rose oxide, romilat, irotyl and floramat alone or in mixtures.

Dyes which can be used are the substances which are approved and suitable for cosmetic purposes. These dyes are normally used in concentrations of from 0.001 to 0.1% by weight, based on the total mixture.

EXAMPLES

The role of cAMP in hair follicle cells is not known. Based on the assumption that it inhibits the differentiation of matrix cells and that it inhibits cellular proliferation the working model underlying the following experiments is based on the demonstration of reduction of proliferation and on the inhibition of the hair shaft production. This model was validated with a well known activator of adenyl cyclase, forskolin. Forskolin has been used to carry out comparison experiments.

Example 1

Extract of *Gymnema Sylvestre*

*Gymnema sylvestre* standardized dry extract (25% in gymnemic acid, saponins, triterpens) is furnished directly by the supplier. It also contains phenolic acids and flavonoids. The supplier is: INDO WORLD TRADING CORPORATION.

The standardized dry extract is obtainable by extracting the leaves of the plant *Gymnema sylvestre* with water, or with alcohols or with mixtures of water and alcohols. The extract is standardized so that its content in gymnemic acids is 25 weight-%. This extract further contains derivatives of quercetol and acids derived from p-coumarine and phenol and vanillic acids and sinapic acids.

Example 2

Anti-Proliferative Activity on Cell Cultures of Human Keratinocytes

The objective of this experiment was to find a suitable screening method for hair growth inhibition. The screening was based on the measurement of the proliferation of the cells in the test stimulated by Epidermal Growth Factor (EGF) in the presence of potential anti-hair-growth substances.

The efficiency was evaluated after incubation of human keratinocytes during 72 hours in the presence of the tested substances and was expressed as a percentage of inhibition of protein level. The protein level was evaluated according to Bradford's method (Bradford, Anal. Biochem., volume 72, pages 248 to 254 (1977)).

TABLE 1

Evaluation of the anti-proliferative activity of the extracts specified in the table on human keratinocytes (cell line A431) on the survival of the keratinocytes (the keratinocytes are incubated for 72 hours and the capacity of the keratinocytes to survive is assessed) (the results are given in percent of the control level)

| Tested product | Control | EGF at 10 ng/ml | EGF + Tested concentrations | | |
|---|---|---|---|---|---|
| | | | 0.003% | 0.01% | 0.03% |
| standardized extract of *Gymnema sylvestre* | 100 | 210 ± 4 | 151 ± 47 | 101 ± 20 | 5 ± 2 |

In the presence of both plant extracts, the proliferative activity of keratinocytes A 431 was reduced. The same results (i.e. inhibition of proliferation) were obtained when the keratinocytes were incubated with the substances in the absence of EGF.

Example 3

Inhibition of Hair Growth

The method of in vitro culture of human hair follicles in an appropriate growth medium (William's E medium) was used for the demonstration of the inhibitory effect on undesired hair growth (Philpott et al: J Cell Sci, volume 97, pages 463 to 471 (1990)). The hair follicles were incubated for 7 days at 37° C. under an atmosphere of air that was enriched with carbon dioxide (5 vol.-%). The length of hair follicles was monitored before being cultured, after 3 days of culture and after 7 days of culture. The growth medium contained or did not contain IGF-1 (Insuline-like growth factor), cytokine that stimulates the hair follicle growth. The test was done on hair follicles coming from 3-5 different donors. For each donor 10 follicles were cultured for each set of conditions.

The results presented in table 2 are the cumulated results of all hair follicles.

TABLE 2

Hair follicles growth - increase in hair growth (in %) after 3 and 7 days of incubation referring to day 0 in the presence of a standardized extract of *Gymnema sylvestre* (5 donors)

| Follicle treatment | IGF-1 (30 ng/ml) | Concentration % w/v | Day 3/ Day 0 | Day 7/Day 0 |
|---|---|---|---|---|
| Control | − | 0 | +25% | +44% |
| *Gymnema sylvestre* standardized extract | − | 0.01 | +28% | +31% |
| Control | + | 0 | +36% | +58% |
| *Gymnema sylvestre* standardized extract | + | 0.01 | +34% | +37% |

% w/v means % weight by volume (1% w/v = 1 g per 100 ml)

The results demonstrate clearly the hair growth reducing activity of the extract of *Gymnema sylvestre* with a definite quantity of gymnemic acid but containing also other components such as phenolic acids and flavonoids. All these components may be responsible for the hair-growth inhibiting effect.

The same type of results as shown in table 3 have been obtained for titrated extracts of *Gymnema sylvestre* from different suppliers with different contents of gymnemic acids. These results are summarized in the following table

| Follicle treatment | IGF-1 (30 ng/ml) | Concentration % P/v | Day 3/ Day 0 | Day 7/ Day 0 |
|---|---|---|---|---|
| Results from other suppliers (only 10 follicles from 1 donor per treatment) | | | | |
| Control | − | 0 | +8% | +38% |
| standardized extract of *Gymnema sylvestre* (25% of gymnenic acid) - Supplier 2 | − | 0.01 | +4% | +4% |
| standardized extract of *Gymnema sylvestre* (25% of gymnenic acid) - Supplier 3 | − | 0.01 | +15% | +19% |
| Control | + | 0 | +21% | +80% |
| standardized extract of *Gymnema sylvestre* (25% of gymnenic acid) - Supplier 2 | + | 0.01 | +7% | +9% |
| standardized extract of *Gymnema sylvestre* (25% of gymnenic acid) - Supplier 3 | + | 0.01 | +13% | +18% |
| Comparison: results with Forskolin (50 follicles from 5 donors per treatment) | | | | |
| Control | − | 0 | +15% | +34% |
| Forskolin | − | 0.001 | +8% | +15% |
| Control | + | 0 | +21% | +43% |
| Forskolin | + | 0.001 | +9% | +17% |

What is claimed is:

1. A method for treating hair growth in a mammal, comprising administering to a mammal in need thereof a composition which inhibits hair growth comprising an effective amount of an aqueous and/or alcoholic extract of leaves of the plant *Gymnema sylvestre*.

2. The method according to claim 1, wherein the mammal is a human.

3. The method according to claim 1, wherein the composition is topically applied.

4. The method of claim 1, wherein the extract is prepared by
   a) extracting the leaves with a solvent selected from the group consisting of water, an alcohol with 1 to 6 carbon atoms, a 1,2-alkanediol and mixtures thereof to obtain a mixture comprising said solvent and the extract, and
   b) removing said solvent from said mixture to obtain the extract.

5. The method of claim 4, wherein the solvent is water.

6. The method of claim 4, wherein the solvent is an alcohol with 1 to 6 carbon atoms.

7. The method of claim 4, wherein the solvent is a 1,2-alkanediol.

* * * * *